(12) United States Patent
Moran et al.

(10) Patent No.: US 12,053,600 B2
(45) Date of Patent: *Aug. 6, 2024

(54) INTRODUCER SET

(71) Applicant: Abiomed Europe Gmbh, Aachen (DE)

(72) Inventors: Adrian Moran, Ballinfull (IE);
Thorsten Siess, Aachen (DE); Walid Aboulhosn, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 662 days.

This patent is subject to a terminal disclaimer.

(21) Appl. No.: 17/062,698

(22) Filed: Oct. 5, 2020

(65) Prior Publication Data

US 2021/0085843 A1 Mar. 25, 2021

Related U.S. Application Data

(63) Continuation of application No. 15/540,598, filed as application No. PCT/EP2016/050235 on Jan. 7, 2016, now Pat. No. 10,835,651.

(30) Foreign Application Priority Data

Jan. 7, 2015 (EP) ..................................... 15150306

(51) Int. Cl.
*A61M 25/06* (2006.01)
*A61M 25/00* (2006.01)
(Continued)

(52) U.S. Cl.
CPC ...... *A61M 25/10182* (2013.11); *A61M 25/00* (2013.01); *A61M 25/0021* (2013.01);
(Continued)

(58) Field of Classification Search
CPC ................ A61M 1/10; A61M 25/0021; A61M 25/0043; A61M 29/00; A61M 29/02; A61M 2025/0293; A61M 2025/0059
See application file for complete search history.

(56) References Cited

U.S. PATENT DOCUMENTS 5,322,511 A * 6/1994 Armbruster ............. A61M 5/20
604/152
5,931,842 A 8/1999 Goldsteen et al.
(Continued)

FOREIGN PATENT DOCUMENTS

EP 0446932 A2 9/1991
EP 2452718 A1 5/2012
(Continued)

OTHER PUBLICATIONS

European Search Report, EP 15150306, dated Jun. 29, 2015.
(Continued)

*Primary Examiner* — Chelsea E Stinson
*Assistant Examiner* — Anh Bui
(74) *Attorney, Agent, or Firm* — Botos Churchill IP Law LLP

(57) ABSTRACT

An introducer set (1) for providing vascular access in a patient's body comprises an Introducer sheath (10) and a dilator (20). The introducer sheath (10) has a tubular body (11) made of flexible material with a distal portion (12), a proximal portion (13) and an inner surface, the proximal portion (13) being configured to be inserted into a patient's vessel to allow a medical device (100) to be inserted through the introducer sheath (10) into the patient's vessel. The tubular body (11) of the introducer sheath has a wall thickness (d) of 0.3 mm or less. The dilator (20) has a body (21) with a proximal portion (23), a distal portion (22) and an outer surface, the dilator (20) being insertable into the introducer sheath (10) such that its proximal portion (23) extends proximally of the introducer sheath (10) when the dilator (20) is inserted in the introducer sheath (10). At least one of the dilator (20) and the introducer sheath (10) comprises a stiffening structure (25) imparting stiffness to the tubular body (11) of the introducer sheath (10), wherein (Continued)

said stiffening structure (25) can be released, removed or otherwise deactivated.

14 Claims, 17 Drawing Sheets

(51) Int. Cl.
    *A61M 25/02*      (2006.01)
    *A61M 25/10*      (2013.01)
    *A61M 29/00*      (2006.01)
    *A61M 29/02*      (2006.01)

(52) U.S. Cl.
    CPC ...... *A61M 25/0043* (2013.01); *A61M 25/005* (2013.01); *A61M 25/02* (2013.01); *A61M 25/0662* (2013.01); *A61M 29/00* (2013.01); *A61M 29/02* (2013.01); *A61M 2025/0059* (2013.01); *A61M 2025/0063* (2013.01); *A61M 2025/0293* (2013.01)

(56) References Cited

U.S. PATENT DOCUMENTS 7,892,162 B1 *    2/2011    Jeevanandam ..... A61M 60/843
                                                              600/18
2005/0131343 A1 *    6/2005    Abrams ............ A61M 25/0662
                                                              606/41
2006/0271085 A1 *    11/2006    Siess ................... A61M 60/216
                                                              606/191
2013/0317476 A1      11/2013    Searle et al.
2014/0171914 A1      6/2014    Rowe et al.

FOREIGN PATENT DOCUMENTS

| JP | H05443 U | 1/1993 |
|---|---|---|
| JP | H0686823 A | 3/1994 |
| JP | 2006520626 A | 9/2006 |
| JP | 2014198262 A | 10/2014 |
| WO | 2009140546 A2 | 11/2009 |

OTHER PUBLICATIONS

International Search Report, PCT/EP2016/050235, dated May 20, 2016.

Office Action in JP Application No. 2017-536239, dated Nov. 29, 2019 with English translation.

Office Action from corresponding Chinese Application No. 202110344694.0 dated Jul. 11, 2022 (24 pages).

Office Action from corresponding Korean Application No. 10-2017-7021924 dated Sep. 30, 2022 (6 pages).

* cited by examiner

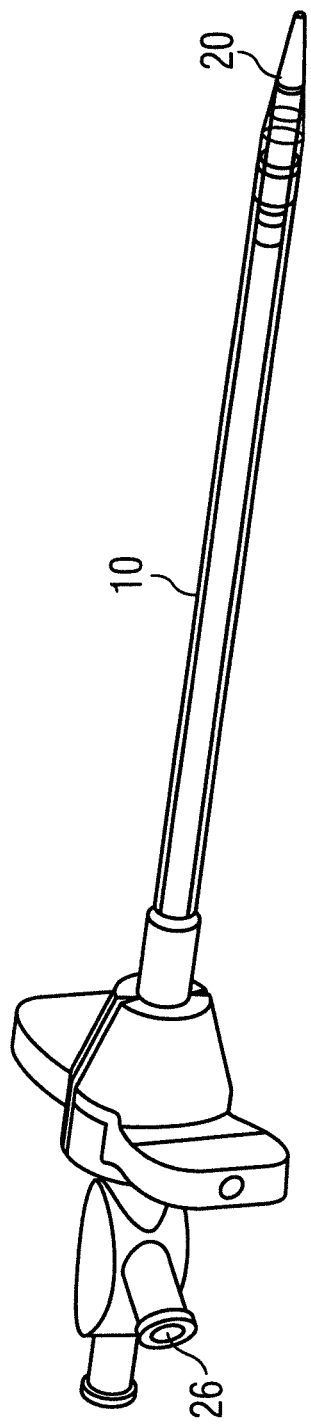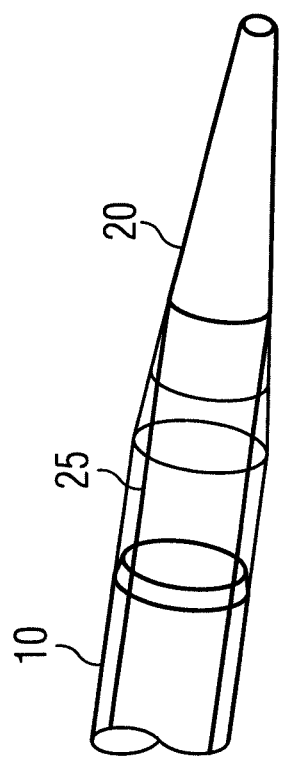
FIG 6a
FIG 6b

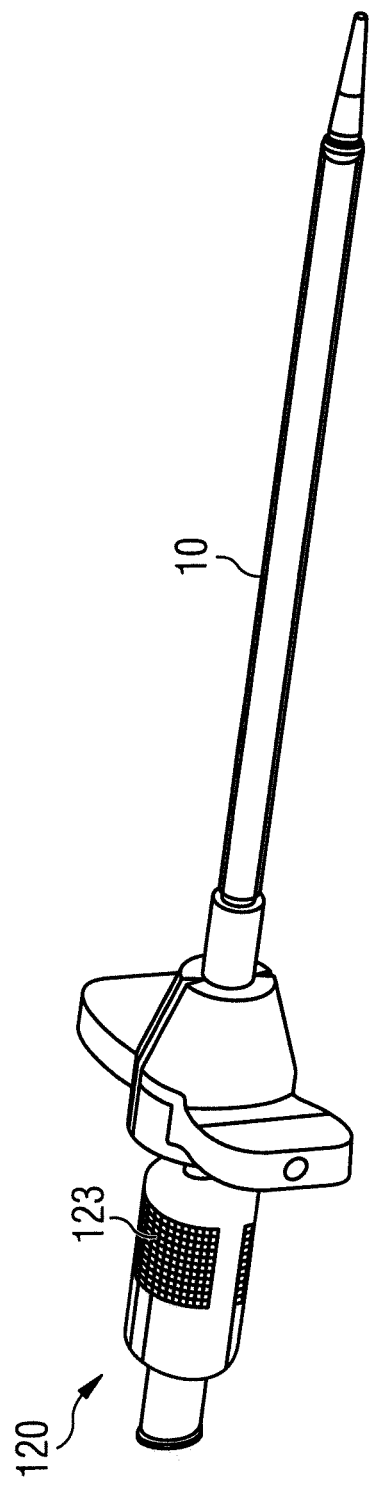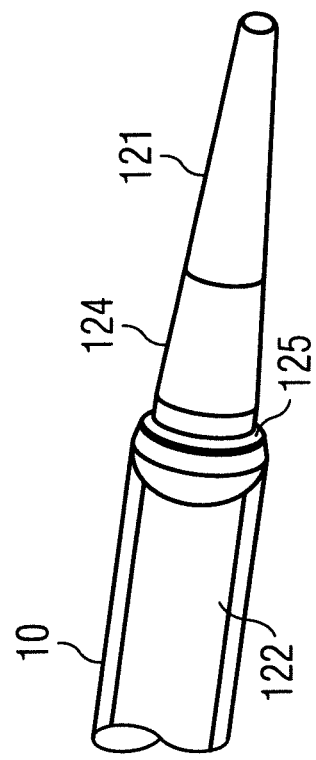

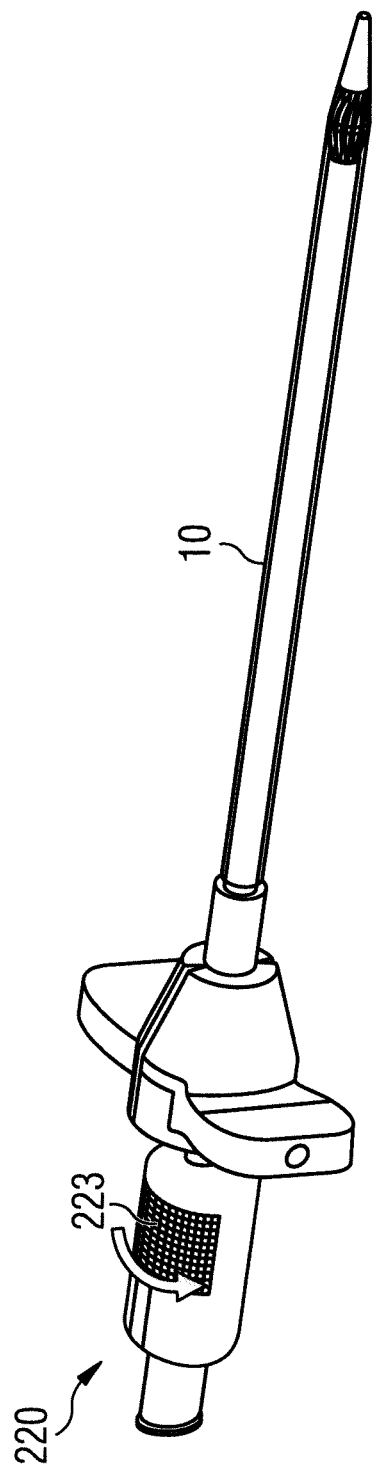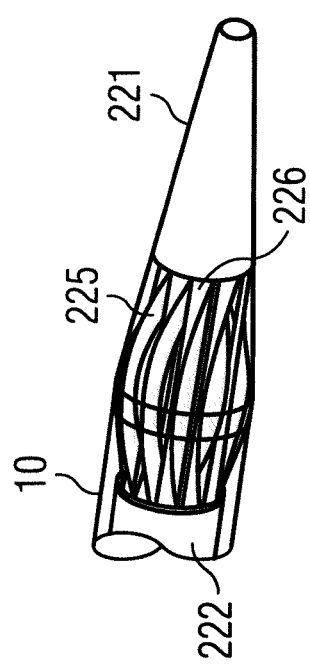
FIG 10a
FIG 10b

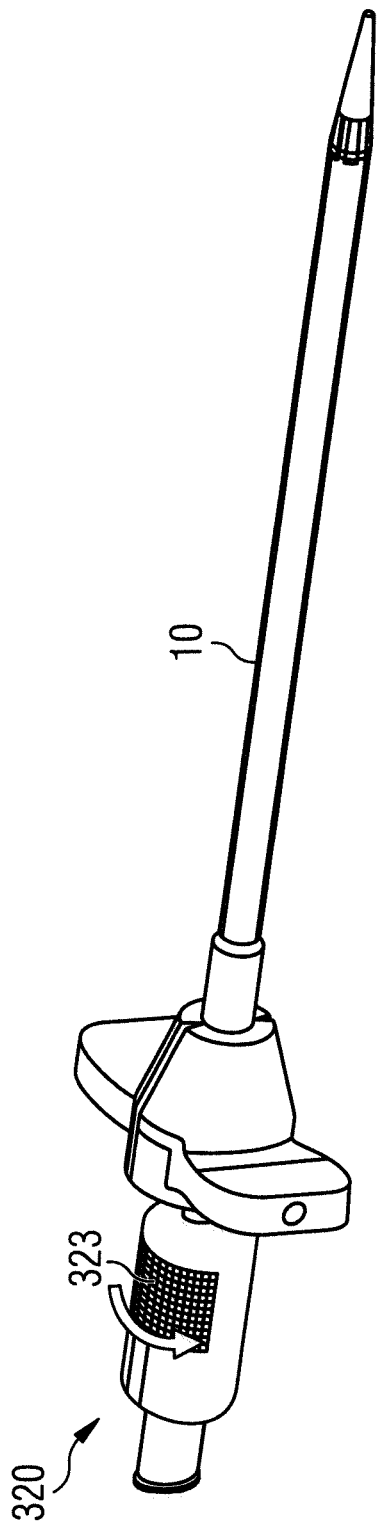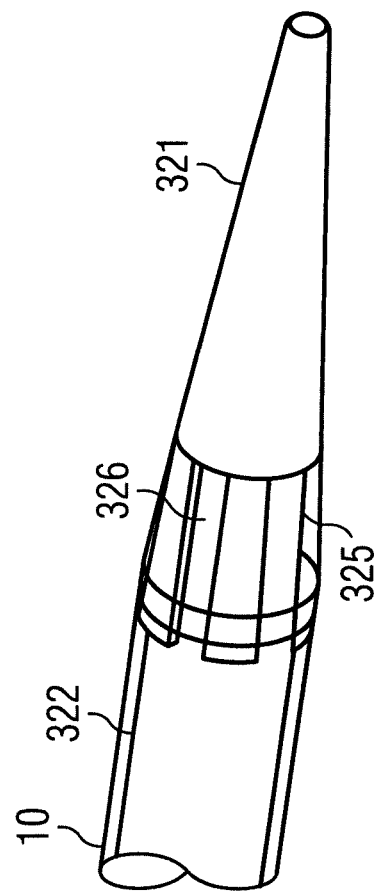
FIG 12a
FIG 12b

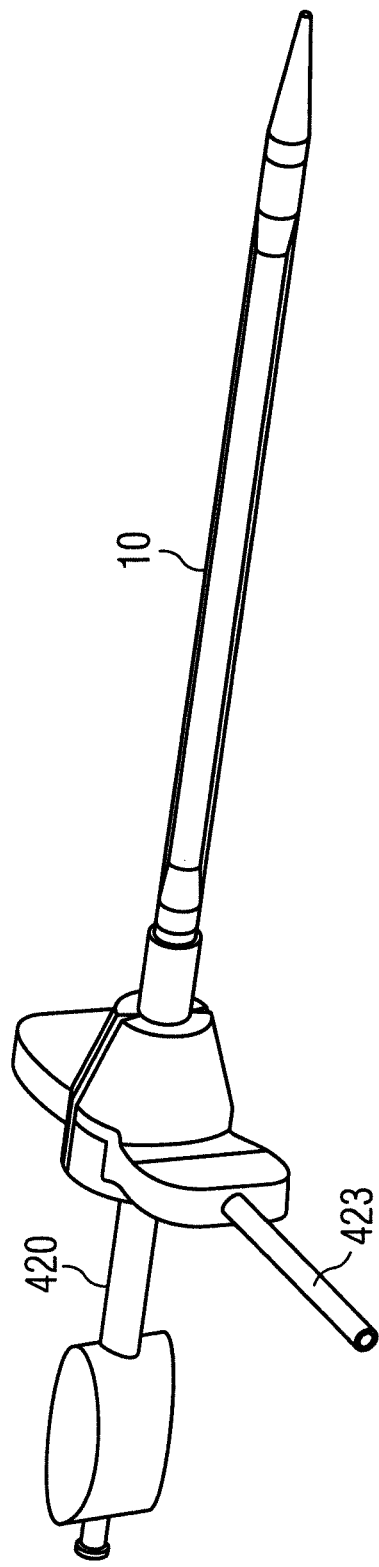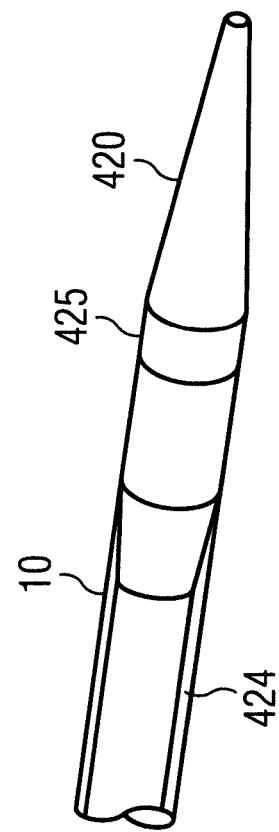

INTRODUCER SET

CROSS-REFERENCE TO RELATED APPLICATIONS

This application is a continuation of U.S. patent application Ser. No. 15/540,598, filed Jun. 29, 2017, and published as U.S. Published Patent Application No. 2018/0001003 A1, now U.S. Pat. No. 10,835,651, which is a U.S. National Stage filing under 35 U.S.C. § 371 of International Application No. PCT/EP2016/050235, filed Jan. 7, 2016, which claims the benefit of European Patent Application No. 15150306.7, filed Jan. 7, 2015, the contents of each of which are hereby incorporated by reference herein in their entirety. International Application No. PCT/EP2016/050235 was published under PCT Article 21(2) in English.

BACKGROUND

Long term vascular access is a common medical procedure used in several medical situations including dialysis for patients requiring frequent dialysis treatments, chemotherapy treatment or ventricular assist device use. Different devices and different methods are used depending on patient needs. Long term vascular access in patients needing ventricular assist devices is common through an open chest procedure and direct cardiovascular access.

Lately there has been a move toward the use of peripheral vessels to access the cardiovascular system in order to avoid traumatic open chest surgery. The move toward the use of peripheral vessels instead of central cardiovascular vessels has been accompanied by the development of a large number of specific devices and tools that are specifically designed for peripheral use. Vascular introducers are the most common devices that have been developed to allow peripheral vascular access. For providing access to a vessel, an introducer sheath usually is directly pierced into a vessel, in particular with the help of a dilator. These introducer sheaths have been limited to small diameters ranging from 1 to 3 mm.

The diameter of the introducer sheath is a limiting factor in providing vascular access. On the one hand, the outer diameter is limited depending on the patient and the vessel that is intended to be accessed. Introducer sheaths having diameters that are too large cannot be introduced into the vessel or may cause harm to the patient, which can lead to severe bleeding. On the other hand, the introducer sheath must provide a minimum inner diameter to allow a medical device such as a catheter or a catheter with an axial blood pump to pass therethrough into the patient's vessel. For instance, a medical device with a dimension of 14 French would require a conventional introducer sheath with a dimension of 16 or 17 French.

SUMMARY OF THE INVENTION

It is an objective of the present invention to provide an introducer set for providing access to a patient's vessel, wherein the access allows the introduction and/or removal of large diameter devices in a safe and controlled manner and by a simple procedure, wherein the diameter of the devices to be introduced can be maximized while the size of the access in the patient's body is minimized.

The invention is described in the accompanying independent claims, with preferred embodiments being specified in the dependent claims.

According to one embodiment of the invention, an introducer set for providing vascular access in a patient's body is provided. The introducer set comprises an introducer sheath and a dilator. The introducer sheath has a tubular body made of flexible material, such as PTFE, with a distal portion, a proximal portion and an inner surface, wherein the proximal portion is configured to be inserted into a patient's vessel to allow a medical device to be inserted through the introducer sheath into the patient's vessel. For instance, the medical device may be a catheter that may be connected to an axial blood pump. The dilator has a body with a proximal portion, a distal portion and an outer surface. The dilator is insertable into the introducer sheath such that its proximal portion extends proximally of the introducer sheath when the dilator is inserted in the introducer sheath. It is to be understood that the term "proximal" refers to directions towards the heart, while the term "distal" refers to directions away from the heart.

The tubular body of the introducer sheath has a wall thickness of 0.3 mm or less, preferably less than 0.2 mm, more preferably less than 0.15 mm, even more preferably less than 0.1 mm. Therefore, the introducer sheath can be denoted as a "thin walled introducer sheath". At least one of the dilator and the introducer sheath comprises a stiffening structure imparting stiffness to the tubular body of the introducer sheath, whereby said stiffening structure can be released, removed or otherwise deactivated.

The thin walled introducer sheath allows the outer dimension of the access to be minimized while its inner dimension is maximized. For instance, introducing a 14 French device only requires a 14.5 French or 15 French introducer sheath. However, such thin walled introducer sheath tends to buckle during insertion into the patient's vessel and during retraction of the dilator. The stiffening structure prevents the thin walled introducer sheath from buckling during insertion into the patient's vessel, when the introducer sheath is placed over a dilator. In particular during retraction of the dilator, however, the stiffening structure should be released, removed or otherwise deactivated to prevent the introducer sheath from buckling and being retracted from the patient's vessel along with the dilator. Releasing the stiffening structure facilitates retraction of the dilator without affecting the introducer sheath. While it is advantageous during insertion into the patient's vessel that the flexible thin walled introducer sheath is supported by the dilator, which is more rigid than the introducer sheath, it is desired that the introducer sheath is released from the dilator during removal of the dilator so that the introducer sheath is left in place in the patient's vessel. Even slight retraction of the introducer sheath would cause problems, because it cannot be pushed back into the patient's vessel without the dilator.

Preferably, the stiffening structure, when activated, causes surface friction between at least a portion of the outer surface of the dilator and at least a portion of the inner surface of the tubular body of the introducer sheath and, when deactivated, causes less or no friction. Increasing and decreasing surface friction between the outer surface of the dilator and the inner surface of the introducer sheath is a simple way to couple and decouple the dilator and the introducer sheath. For instance, when the stiffening structure is deactivated, the body of the dilator may have a first outer diameter which is smaller than an inner diameter of the tubular body of the introducer sheath, and when the stiffening structure is activated, at least a portion, preferably at least a proximal portion, of the dilator may have a second outer diameter larger than the first outer diameter such that the outer surface of the dilator contacts the inner surface of the tubular body of the introducer sheath.

According to another embodiment of the invention, a dilator configured for use in an introducer sheath is provided, preferably in an introducer set as described above. The dilator comprises a body with an outer surface, wherein the dilator is collapsible so as to allow for decreasing a cross-section of the body in order to decrease surface friction between the outer surface and an inner surface of the introducer sheath. The dilator may advantageously be used with a thin walled introducer sheath, wherein an increased surface friction between the dilator and the introducer sheath is preferred during insertion into a patient's vessel, whereas a decreased surface friction is preferred during retraction of the dilator to prevent the introducer sheath from buckling.

According to another embodiment of the invention, an introducer sheath is provided that comprises a tubular body made of a flexible material with a distal portion and a proximal portion, wherein the proximal portion is configured to be inserted into a patient's vessel to allow a medical device to be inserted through the introducer sheath into the patient's vessel. The tubular body of the introducer sheath has a wall thickness of 0.3 mm or less, preferably less than 0.2 mm, more preferably less than 0.15 mm, even more preferably less than 0.1 mm.

A method for providing vascular access in a patient's body is disclosed, wherein an introducer set is provided in a first step. The introducer set comprises an introducer sheath and a dilator. The introducer sheath comprises a tubular body with a distal portion, a proximal portion and an inner surface, the proximal portion being configured to be inserted into a patient's vessel to allow a medical device to be inserted through the introducer sheath into the patient's vessel. The tubular body of the introducer sheath has a wall thickness of 0.3 mm or less. The dilator comprises a body with a proximal portion, a distal portion and an outer surface. The dilator is inserted in the introducer sheath such that the proximal portion extends proximally out of the introducer sheath, the dilator comprising a deflatable balloon for decreasing surface friction between at least a portion of the outer surface of the dilator and at least a portion of the inner surface of the tubular body of the introducer sheath.

After insertion of the introducer sheath and the dilator into a vessel of a patient, the balloon is deflated and the dilator is retracted from the introducer sheath such that the introducer sheath is left behind in the patient's vessel. Deflating the balloon before retraction of the dilator prevents the introducer sheath from being retracted from the patient along with the dilator and from buckling. According to an embodiment, it may be required to insert the dilator into the introducer sheath and to inflate the balloon of the dilator before inserting the introducer sheath and the dilator into the patient's vessel. Inflating the balloon causes the dilator to contact the inner surface of the introducer sheath to provide sufficient stiffness and to prevent the introducer sheath from buckling during insertion into the patient's vessel.

In a preferred embodiment, the stiffening structure comprises a deflatable balloon. The balloon may be arranged at least in the proximal portion of the dilator body, preferably along substantially an entire length of the dilator body. It may be sufficient to provide the balloon at least in the proximal portion of the dilator body. However, in order to increase stability and stiffness, the balloon may be provided substantially along the entire length of the dilator body, in particular along a main portion of the dilator body, excluding one or both of a distal tip that may be tapered and a proximal portion that may have a handle or a connection port. The balloon may comprise a non-compliant material, preferably a polyamide, such as Nylon.

In order to be able to deflate and/or inflate the balloon, the dilator may comprise an inflation port at the distal portion of the dilator body that is in fluid communication with the balloon. The inflation port may be connected to a reservoir fillable with a fluid and comprising a pressure device, preferably a syringe-type pressure device, such that a fluid received in the reservoir can be pressurized to inflate the balloon. The pressure device may comprise a plunger which is sealed against an inner wall of the reservoir and has a first thread. The pressure device may further comprise an actuating screw having a second thread mating with the first thread such that the plunger can be moved within the reservoir to pressurize fluid received in the reservoir by rotation of the actuating screw. The pressure device provides a simple mechanical device to control the pressure in the balloon and thus the outer diameter of the dilator.

In another embodiment, the stiffening structure may comprise first and second elements that are translatable with respect to each other, and an actuating mechanism for translating at least one of the first and second elements with respect to the other in a longitudinal direction of the dilator. Preferably, rotation of the actuating mechanism causes such longitudinal translation. The second element may have a tubular body and the first element may extend through the tubular body of the second element beyond a proximal end of the second element.

This stiffening structure may comprise at least one deformable member engaging the first and second elements such that said longitudinal translation causes a decompression of the deformable member in the longitudinal direction of the dilator and thereby a radial reduction of the deformable member. Preferably, the deformable member forms part of the dilator and, in an uncompressed state, has substantially the same diameter as the body of the dilator.

The deformable member may be ring-shaped or tubular-shaped and may comprise a soft polymer, preferably a silicone. In another embodiment, the deformable member may comprise a plurality of slits extending in the longitudinal direction of the dilator to allow the deformable member to radially collapse upon said longitudinal decompression. In another embodiment, the deformable member may be attached to the first element and engage the second element, wherein the deformable member may comprise a plurality of tabs slidable on a ramped end portion of the second element to radially deform when the second element is longitudinally translated. The deformable member may be formed separately from or integrally with at least one of the first and second elements of the stiffening structure.

According to another preferred embodiment, the introducer sheath may comprise a hydraulic port that is in fluid communication with a space defined by the inner surface of the introducer sheath and the outer surface of the dilator. In order to stiffen and support the thin walled introducer sheath, a hydraulic fluid is pressed into the space, which preferably is substantially fluid tight at the proximal end, in particular at a location where the proximal end of the introducer sheath contacts the dilator. The tight connection may be maintained until a certain pressure in the space between the dilator and the introducer sheath is exceeded. In order to release the introducer sheath from the dilator, the pressure of the hydraulic fluid is further increased such that the fluid leaks at the proximal end of the introducer sheath and causes a gap with a fluid film between the dilator and the introducer sheath. The dilator can then be retracted easily without buckling the introducer sheath. The hydraulic fluid may be physiological saline, which does not cause harm to the patient when it flows into the patient's vessel.

According to another embodiment, the tubular body of the introducer sheath may comprise at least one cavity extending in the longitudinal direction of the tubular body and accommodating a removable supporting strut. At least one, preferably a plurality, such as two, three, four, five or six, of such supporting struts may be inserted in elongated cavities that are disposed in the wall of the introducer sheath along a longitudinal direction. The supporting struts may be wires or the like. When the supporting struts are not needed any more, they may simply be retracted from the cavities. Removing the struts can increase the inner diameter of the introducer sheath. Preferably, the supporting struts have a cross-section that is different in shape from a cross-section of the cavity to provide low friction between the cavity and the supporting strut, for example a polygonal or star-like cross-sectional shape.

In an embodiment, the introducer sheath comprises a hemostatic valve at its distal portion. The hemostatic valve provides hemostasis. In other words, it seals the distal end of the introducer sheath to prevent blood from flowing through the valve during insertion of a medical device, such as a catheter. The valve may include a membrane that may be constructed as a flexible disk or in another configuration providing the function of a check valve. In order to allow the introducer sheath to be peeled away from a medical device that has been inserted through the introducer sheath into the patient's vessel, the introducer sheath may be separable along its length.

BRIEF DESCRIPTION OF THE DRAWINGS

The foregoing summary, as well as the following detailed description of preferred embodiments, are better understood when read in conjunction with the appended drawings. For the purpose of illustrating the present disclosure, reference is made to the drawings. The scope of the disclosure is not limited, however, to the specific embodiments disclosed in the drawings. In the drawings:

FIGS. 6a and 6b show another embodiment of an introducer set in a condition during insertion into a patient's vessel.

FIGS. 8a and 8b show another embodiment of an introducer set in a condition during insertion into a patient's vessel.

FIGS. 10a and 10b show another embodiment of an introducer set in a condition during insertion into a patient's vessel.

FIGS. 12a and 12b show another embodiment of an introducer set in a condition during insertion into a patient's vessel.

FIGS. 14a and 14b show another embodiment of an introducer set in a condition during insertion into a patient's vessel.

DETAILED DESCRIPTION

Figure 1:
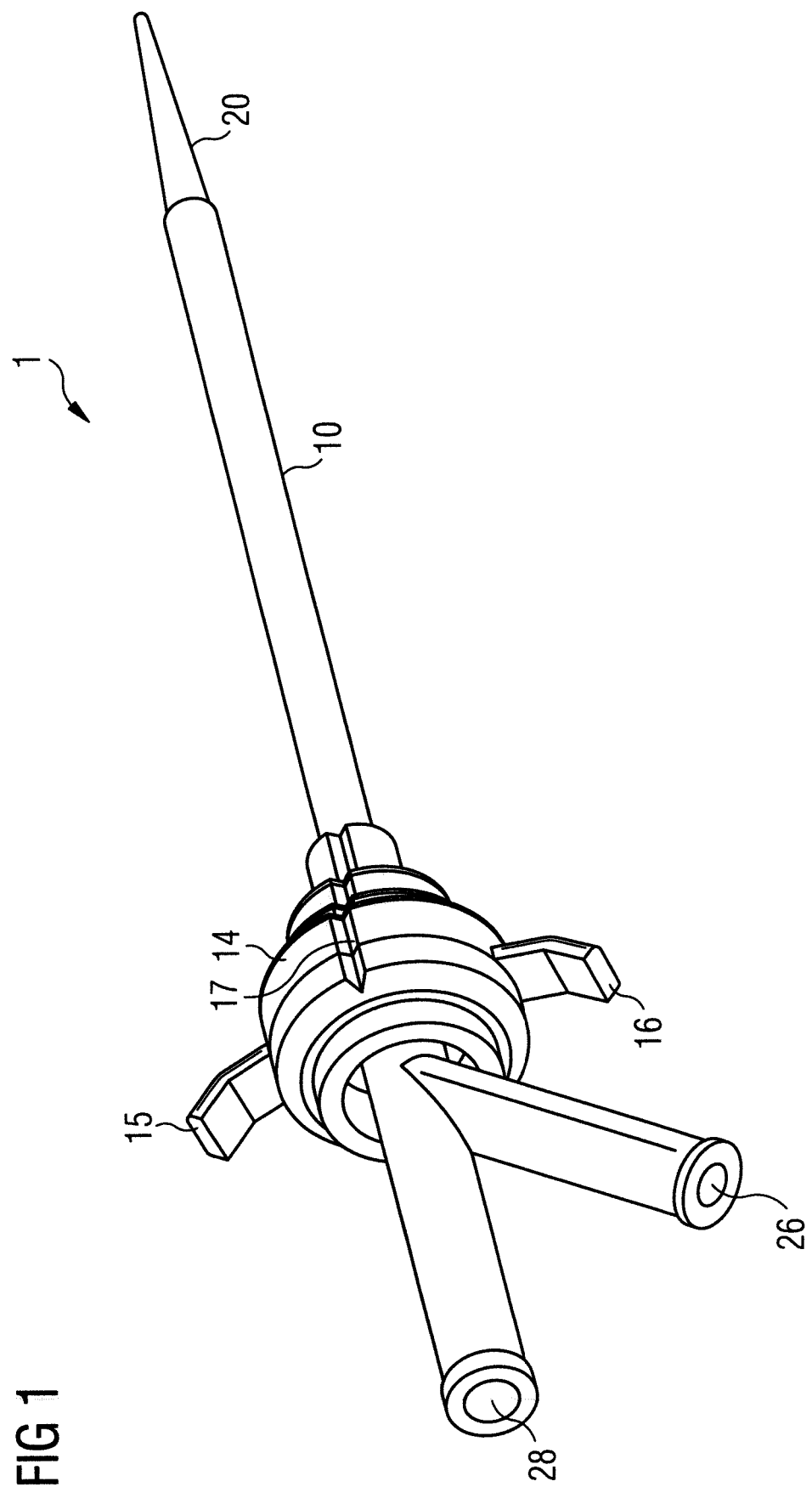
FIG. 1 shows an introducer set comprising a dilator and an introducer sheath according to an embodiment of the invention.
Figure 2:
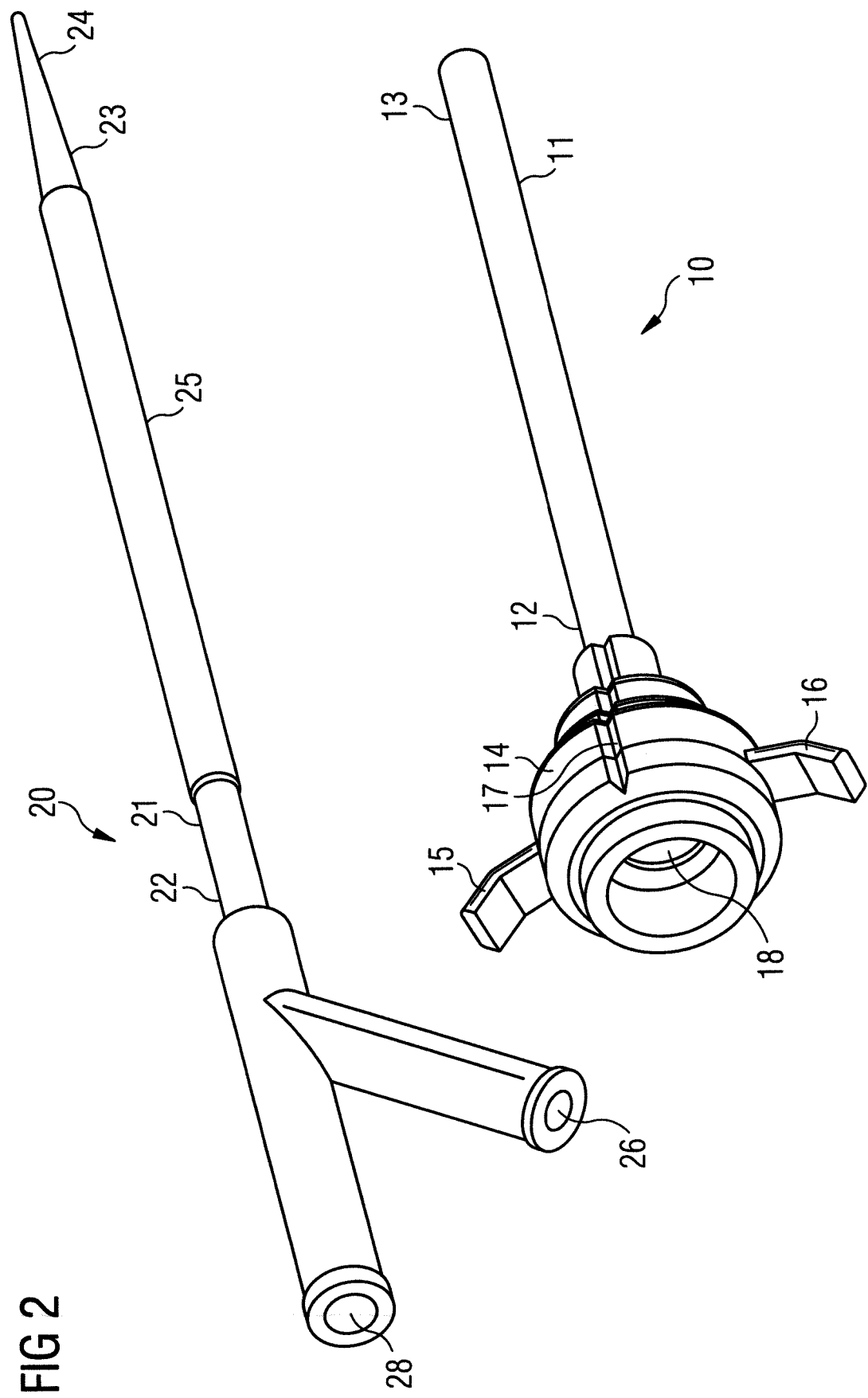
FIG. 2 shows the dilator and the introducer sheath of FIG. 1 separately.
Figure 3:
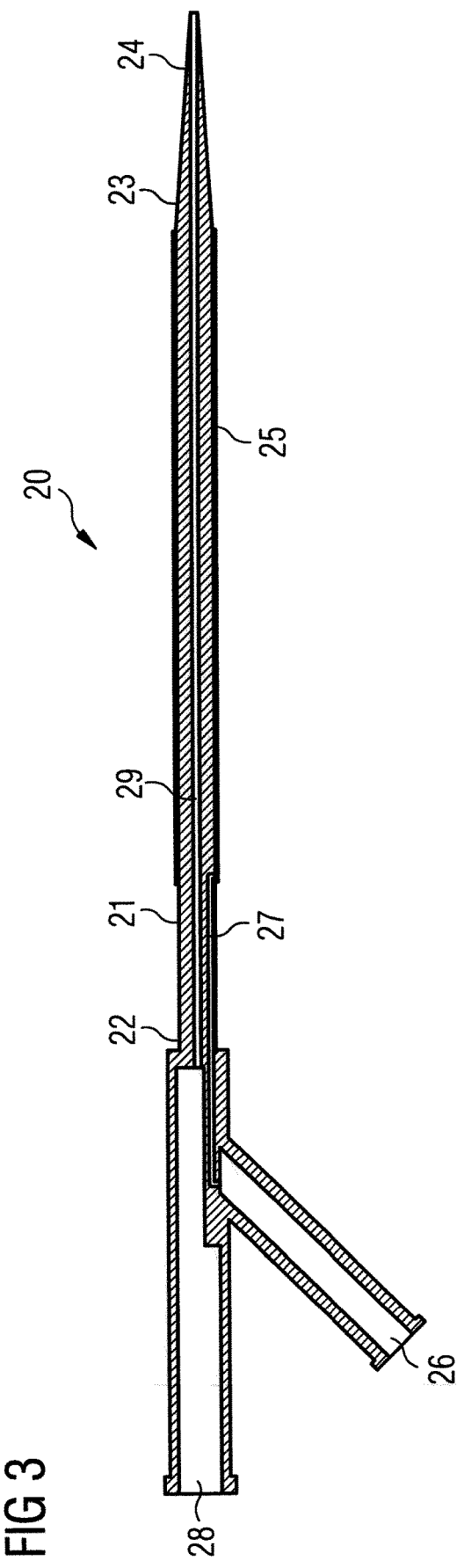
FIG. 3 shows a cross-sectional view of the dilator of FIG. 1.
Figure 4:
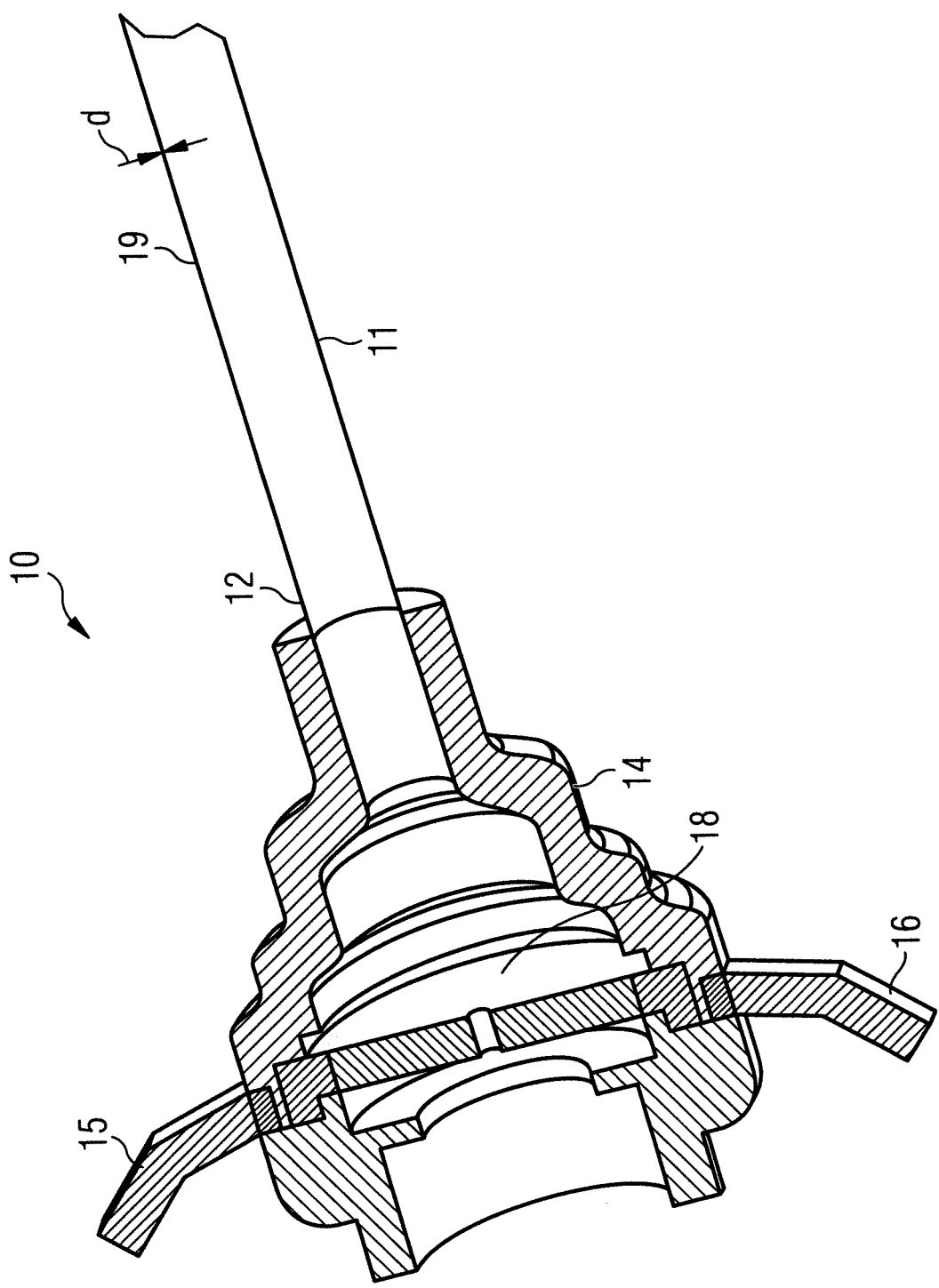
FIG. 4 shows a cross-sectional view of the introducer sheath of FIG. 1.

Referring to FIGS. 1 to 4, different views of an introducer set 1 according to an embodiment of the present invention are shown. The introducer set 1 includes an introducer sheath 10 and a dilator 20, which are shown assembled in FIG. 1 and separately in FIG. 2. The introducer sheath 10 includes a tubular body 11 having a distal portion 12 and a proximal portion 13. A hemostasis valve 14 having a flexible membrane 18 is provided at the distal portion 13. Two handles 15 and 16 are provided for manipulating the introducer sheath 10 and for separating the introducer sheath 10, in particular for splitting the hemostasis valve 14. A longitudinal notch 17 is provided in the hemostasis valve 14 to form a predetermined breaking line. The tubular body 11 of the introducer sheath 10 has a wall 19 with a wall thickness d that is less than 0.3 mm. The introducer sheath 10 is, therefore, a thin walled introducer sheath.

The dilator 20 has a body 21 with a distal portion 22 and a proximal portion 23. The proximal portion 23 includes a tapered tip 24 to facilitate insertion into the patient's vessel. Ports 26 and 28 are provided at the distal portion. The port 28 is connected to an internal lumen 29 that is configured to receive a guide wire therethrough (not shown). In other words, the dilator 20 can be placed over a guide wire that has been inserted into the patient's vessel for example by means of the Seldinger technique. A balloon 25 is disposed on the body 21 of the dilator 20 and extends over a major portion thereof, excluding the tapered tip 24 and the distal-most portion of the body 21. The balloon 25 can be inflated and deflated via the port 26 that is connected to the balloon 25 via a lumen 27 in the distal portion 22 of the body 21. The balloon is made of a non-compliant material such as Nylon.

The balloon 25 of the dilator 20 is utilized as a stiffening structure to support the thin walled introducer sheath 10. The dilator 20 is inserted into the introducer sheath 10 with the balloon 25 deflated. In other words, the balloon is pre-loaded before the operation. A fluid, such as air, is filled into the balloon 25 via the port 26 to inflate the balloon 25 such that the balloon 25 contacts an inner surface of the introducer sheath 10. Surface friction between the dilator 20 and the introducer sheath 10 is thereby increased, which provides stability to the introducer sheath 10 during insertion into the patient's vessel and prevents the introducer sheath 10 from buckling. When the dilator 20 is to be retracted after the assembly has been inserted into the patient's vessel, the balloon 25 is deflated to decrease surface friction between the dilator 20 and the introducer sheath 10. The dilator 20 can then be retracted from the introducer sheath 10 substantially without any interference. The dilator 20 and the introducer sheath 10 can move freely.

Figure 5A:
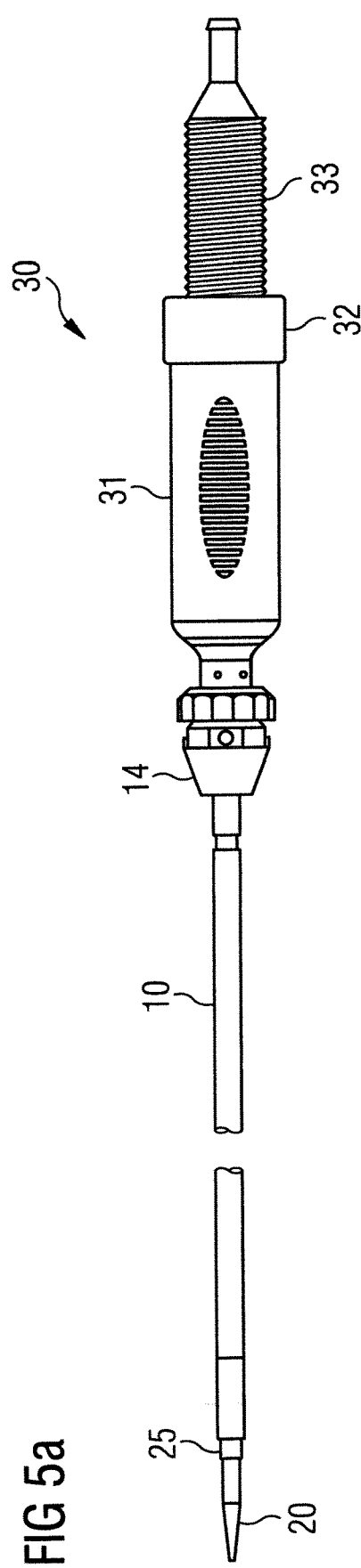
FIGS. 5a and 5b show a side view and a cross-sectional view, respectively, of an introducer set assembled with a pressure device.
Figure 5B:
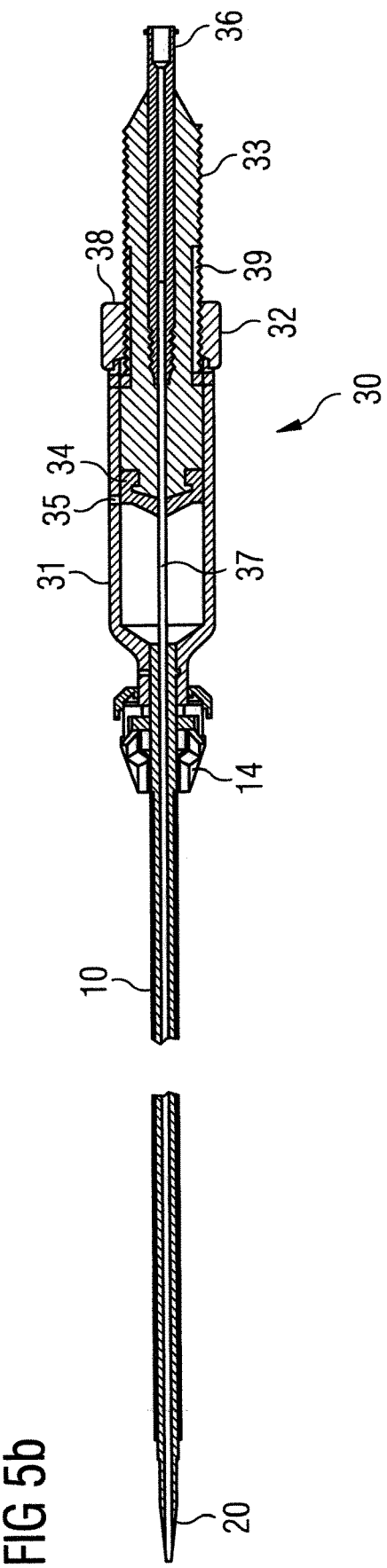

FIGS. 5a and 5b show an embodiment of an introducer set comprising an introducer sheath 10 and a dilator 20 attached to a pressure device 30. The pressure device 30 is connected to the balloon 25 to inflate and deflate the balloon 25. The syringe-type pressure device 30 has a body 31 which forms a reservoir that can be filled with a fluid, such as air, via an aperture 35. A plunger 33 is disposed in the body 31 and sealed against an inner surface of the body 31 by means of a diaphragm seal 34. The plunger 33 is actuated by means of an actuating screw 32. Threads 38 of the screw 32 engage threads 39 on the plunger 33 to translate the plunger 33 when the screw 32 is rotated without rotating the plunger 33. A Luer connector 36 may be provided at the end of the plunger 33 which communicates with a guide tube 37 that may receive a guide wire. The pressure device 30 allows adjustment of the pressure in the balloon 25 and thus of the outer diameter of the dilator 20 by actuation of the screw 32.

Figure 7A:
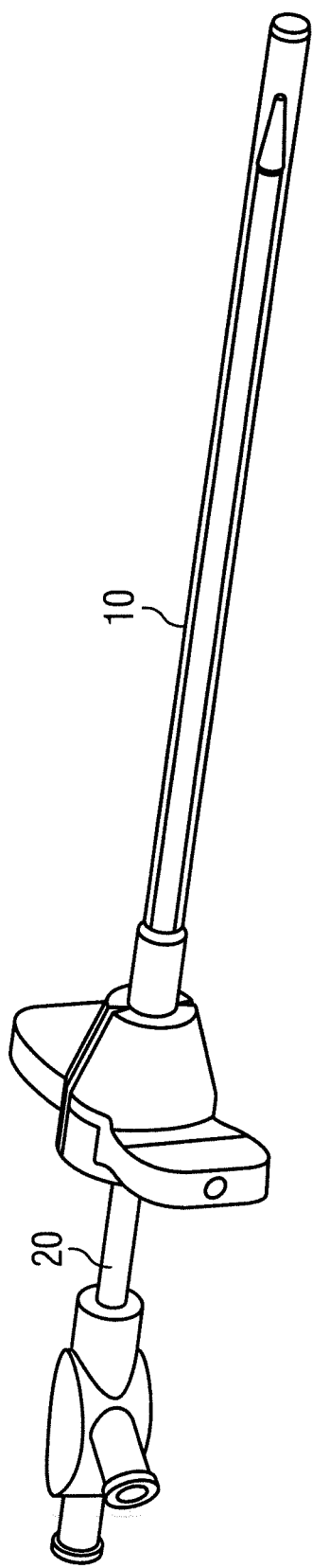
FIGS. 7a to 7c show the introducer set of FIGS. 6a and 6b in a condition during retraction of the dilator.
Figure 7C:
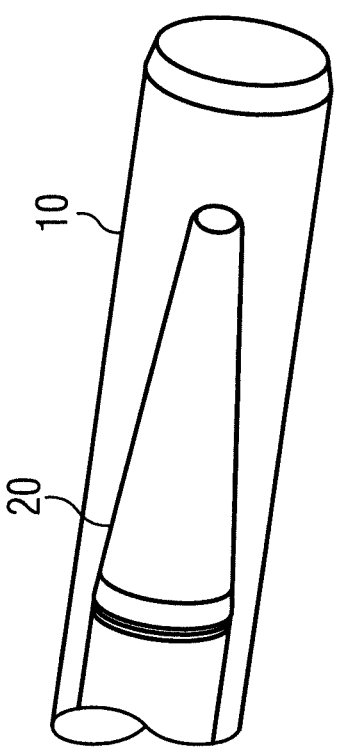
Figure 7B:
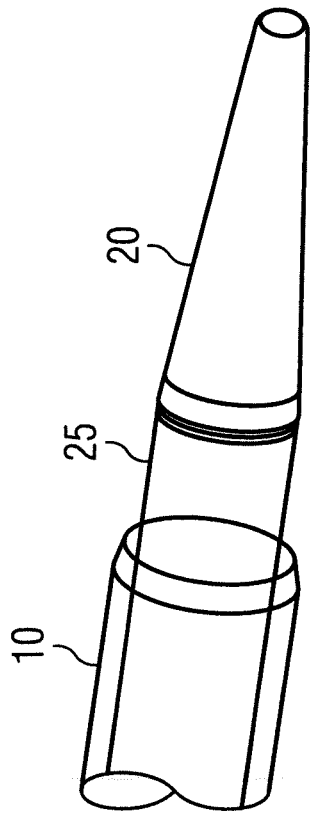
Figure 9A:
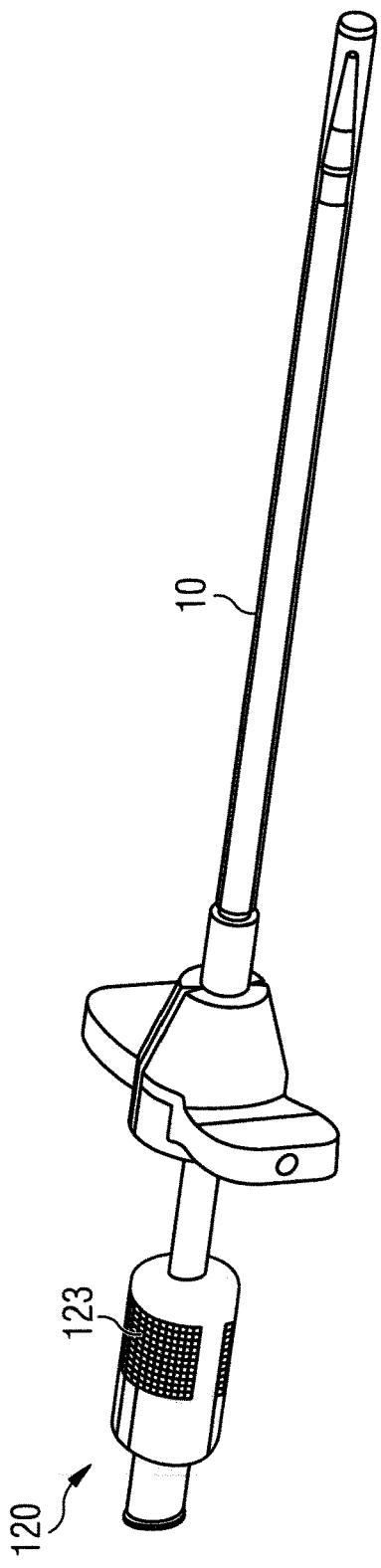
FIGS. 9a to 9c show the introducer set of FIGS. 8a and 8b in a condition during retraction of the dilator.
Figure 9B:
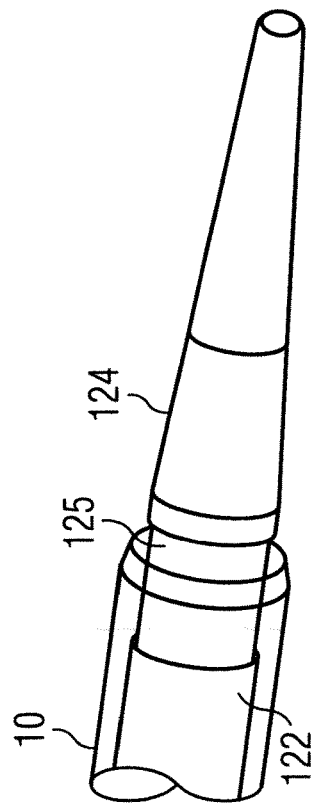
Figure 9C:
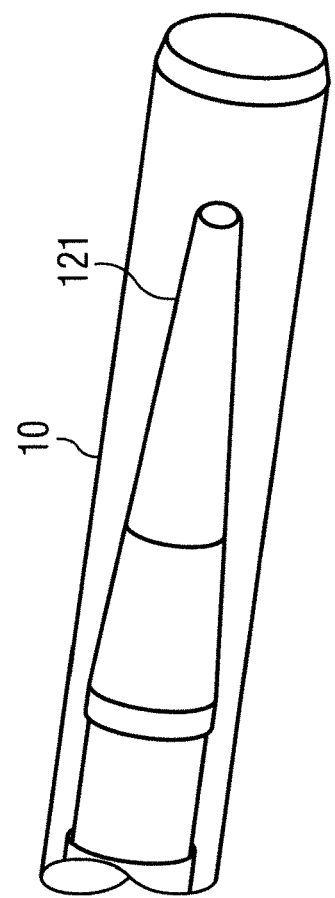
Figure 11A:
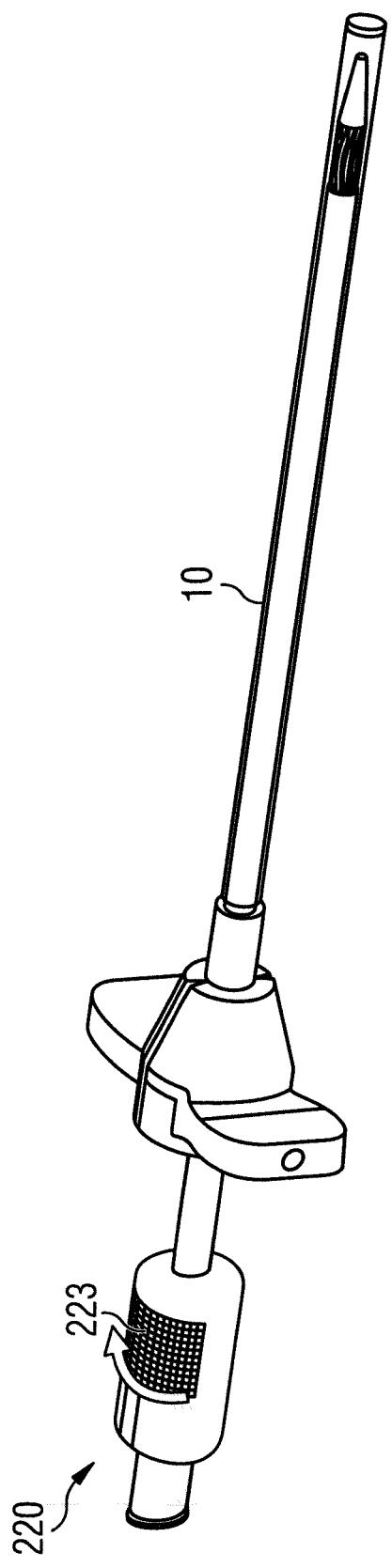
FIGS. 11a to 11c show the introducer set of FIGS. 10a and 10b in a condition during retraction of the dilator.
Figure 11C:
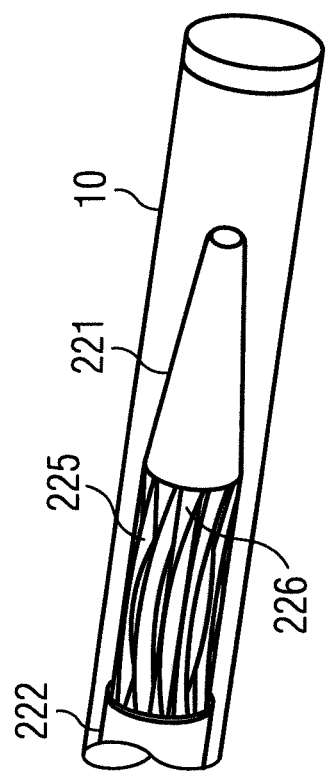
Figure 11B:
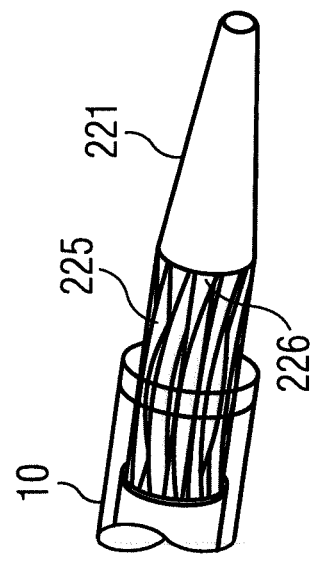

Now referring to FIGS. 6a and 6b, the introducer set is shown with the dilator 20 pre-loaded into the introducer sheath 10. This embodiment is similar to the above-described embodiments and comprises an inflatable balloon 25. As can be seen in FIG. 6b, the balloon 25 is inflated and forms part of a transition between the proximal end of the body 11 of the introducer sheath 10 and the tapered tip 24 of the dilator 20 to ensure a smooth insertion into the patient's vessel. During removal of the dilator 20 the balloon 25 is deflated as shown in FIGS. 7a to 7c. Due to the clearance between the introducer sheath 10 and the dilator 20, the dilator 20 can freely move in the introducer sheath 10 and be retracted substantially without any interference. The balloon 25 may extend only in the proximal portion 23 of the body 21 of the dilator 20 or may extend substantially along the entire length of the body 21.

Another embodiment is shown in FIGS. 8a, 8b and 9a to 9c. In this embodiment, expansion of the diameter of the dilator 120 is not accomplished by an inflatable balloon but by a deformable insert 125 that expands radially upon longitudinal compression. The insert 125 may be made of a soft polymer, such as silicone. The dilator 120 comprises two elements 121 and 122 that are longitudinally translatable with respect to each other. The element 121 forming the tip of the dilator 120 is inserted through the other element 122 which is tubular. A screw mechanism 123 is used to cause the translation of the elements 121 and 122. In particular, the tubular element 122 is advanced proximally. Between two shoulders a ring 124 and the deformable insert 125 are disposed. As can be seen in FIG. 8b, the insert 125 is longitudinally compressed by translating the elements 121 and 122 with respect to each other such that it radially expands and contacts an inner surface of the introducer sheath 10. The introducer sheath 10 is thus clamped and stabilized for insertion into the patient's vessel. In order to remove the dilator 120, the screw mechanism 123 is actuated to release the insert 125 such that it longitudinally relaxes and radially collapses. The dilator 120 can then be removed from the introducer sheath 10 without any interference.

The embodiment shown in FIGS. 10a, 10b and 11a to 11c is similar to the embodiment described in connection with FIGS. 8a, 8b and 9a to 9c. The dilator 220 comprises two elements 221 and 222, wherein the element 222 can be longitudinally translated by actuating a screw mechanism 223. An arrangement comprising longitudinal slits 225 and legs 226 is provided that can be radially expanded similar to the aforementioned silicone insert. As can be seen in FIG. 10b, the slits 225 allow the legs 225 to radially expand when longitudinally compressed. This secures the introducer sheath 10 to the dilator 220 during insertion into the patient's vessel. In order to be able to retract the dilator 220 from the introducer sheath 10, the screw mechanism 223 is actuated to distally translate the element 222 to thereby radially collapse the legs 226. The dilator 220 can then freely move within the introducer sheath 10 such that the introducer sheath 10 is left in the patient's vessel and does not buckle.

Figure 13A:
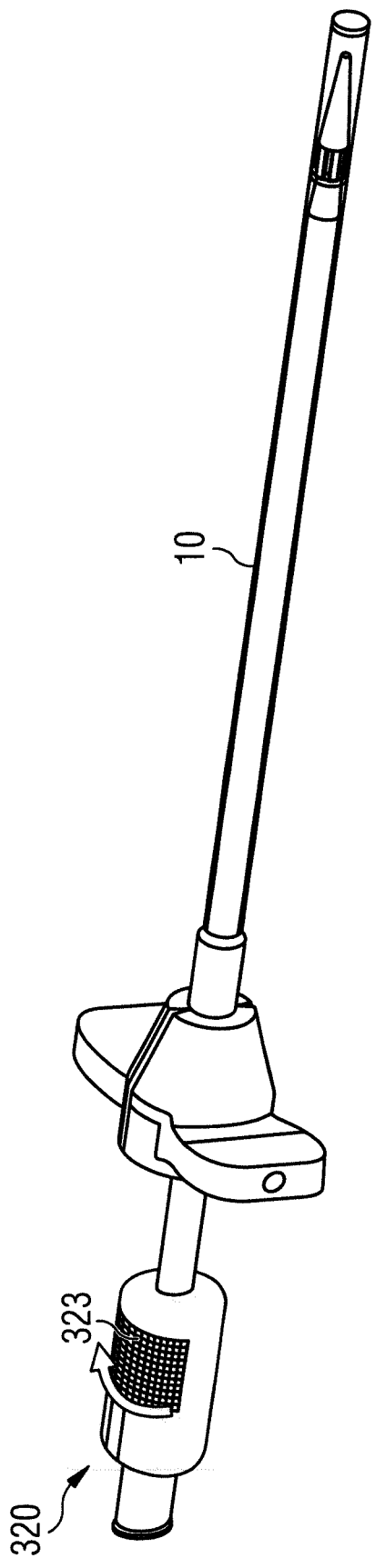
FIGS. 13a to 13c show the introducer set of FIGS. 12a and 12b in a condition during retraction of the dilator.
Figure 13C:
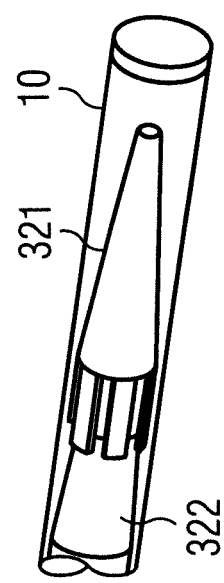
Figure 13B:
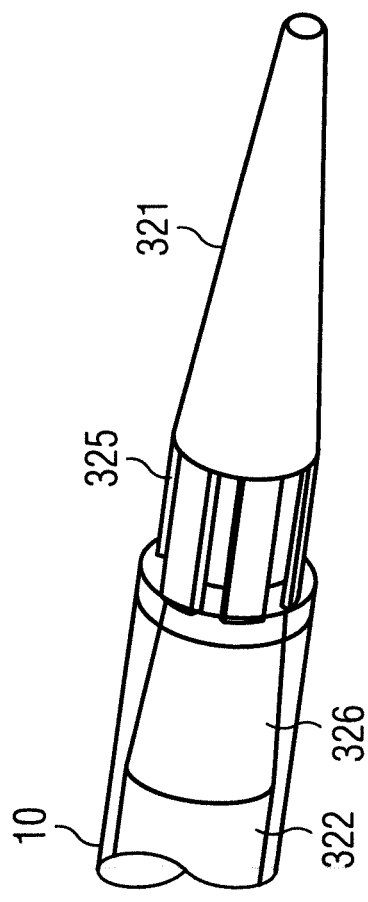
Figure 15A:
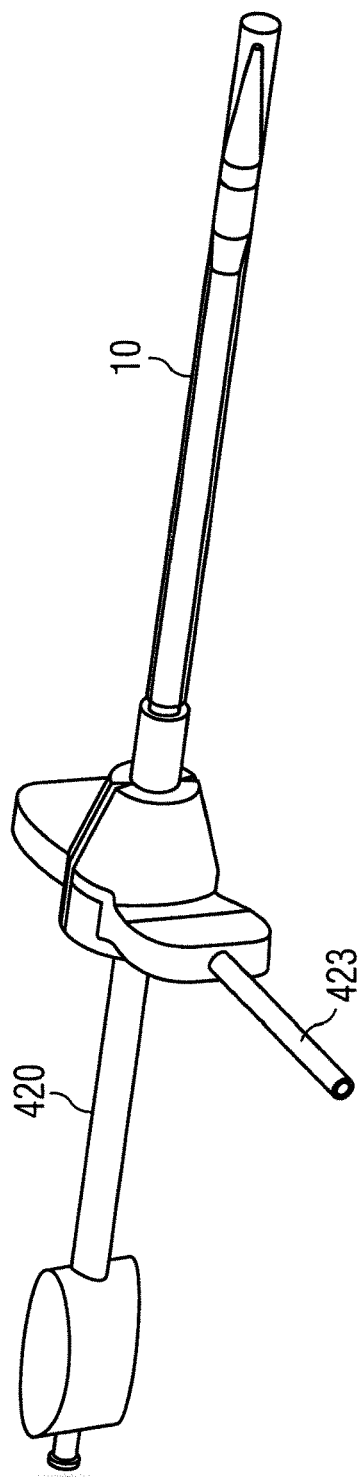
FIGS. 15a to 15c show the introducer set of FIGS. 14a and 14b in a condition during retraction of the dilator.
Figure 15C:
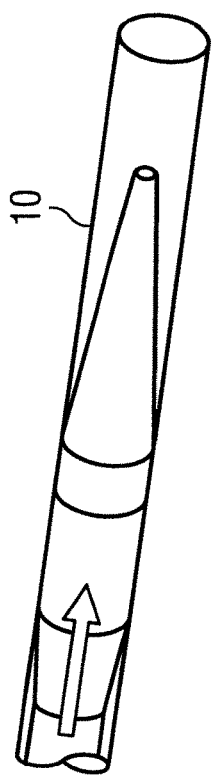
Figure 15B:
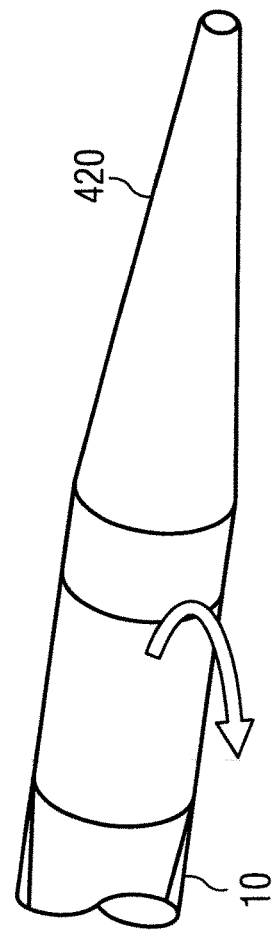

Another embodiment where the dilator 320 has two elements 321 and 322 is shown in FIGS. 12a, 12b and 13a to 13c. A radially expandable arrangement is formed by tabs 325 that are connected to or integrally formed with the element 321 of the dilator 320. As can be seen in FIG. 12b, the element 322 has a ramped proximal end portion 326 such that the tabs 325 radially expand when the element 322 is proximally advanced by actuation of the screw mechanism 323. The tabs 325 then contact the inner surface of the thin walled introducer sheath 10 so as to prevent the introducer sheath 10 from buckling during insertion into the patient's vessel. In FIGS. 13a to 13c, the ramped end portion 326 is retracted distally such that the tabs 325 are radially collapsed to allow free movement of the dilator 320 in the introducer sheath 10 during retraction of the dilator 320.

A further embodiment of an introducer set comprising a thin walled introducer sheath 10 and a dilator 420 is shown in FIGS. 14a, 14b and 15a to 15c. A space or recess 424 is formed between the dilator 420 and the introducer sheath 10 and can be filled with a fluid, such as saline, via a port 423. An enlarged diameter portion 425 of the dilator 420 is provided in the region of the distal end of the introducer sheath 10 to create a tight connection between the dilator 420 and the introducer sheath 10. During insertion into the patient's vessel, the space 424 is filled with a fluid to stabilize the introducer sheath 10. Particularly referring to FIG. 15b, during removal of the dilator 420 the pressure of the fluid is increased to force the fluid to leak at the proximal end of the introducer sheath 10, thereby creating a film layer and a reduced friction between the dilator 420 and the introducer sheath 10, which allows removal of the dilator 420 without buckling of the introducer sheath 10.

Figure 16:
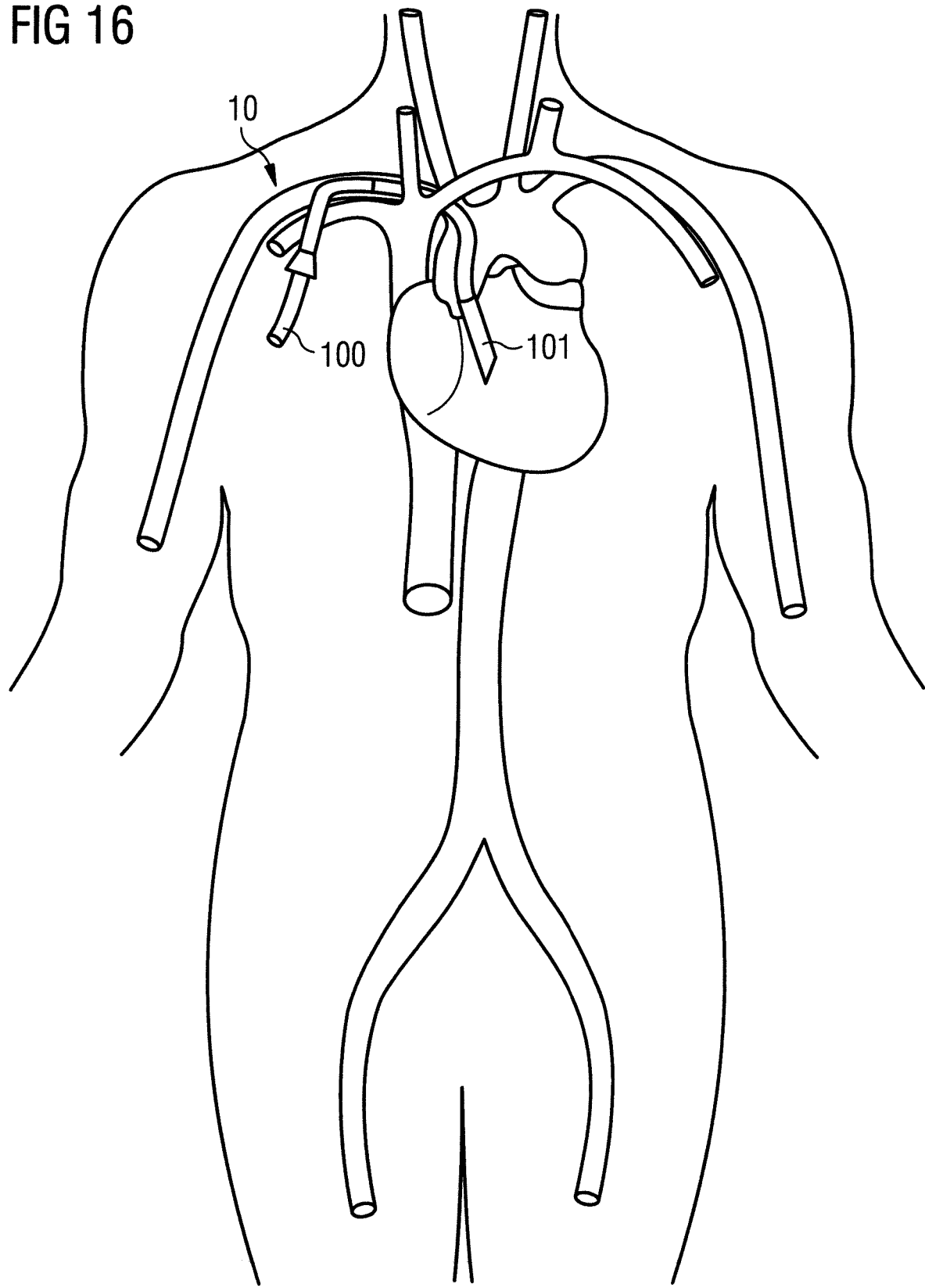
FIG. 16 shows an application of the invention.
Figure 17:
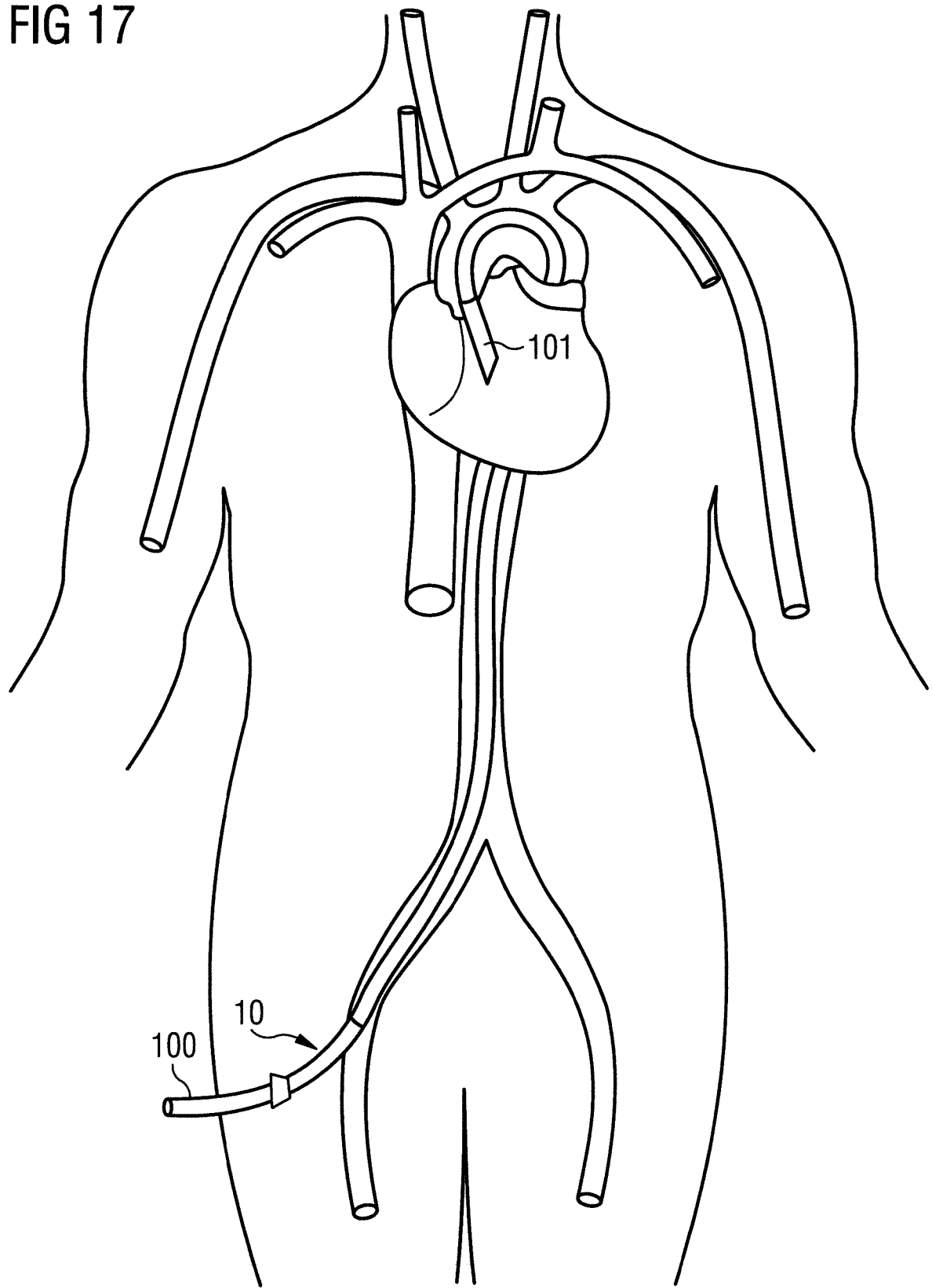
FIG. 17 shows another application of the invention.

Referring now to FIGS. 16 and 17, applications of an introducer set are shown. The introducer set may be in accordance with any one of the above disclosed embodiments. It is used to insert an axial blood pump 101 by means of a catheter 100 through a patient's vessel into the patient's heart to provide a ventricular assistant device. The vascular access may be placed in a peripheral vessel in the patient's thorax (FIG. 16) or in the patient's groin (FIG. 17).

PREFERRED EMBODIMENTS OF THE INVENTION

In the following paragraphs, preferred embodiments of the invention will be disclosed.

1. An introducer set 1 for providing vascular access in a patient's body, comprising:
    an introducer sheath 10 having a tubular body 11 made of flexible material with a distal portion 12, a proximal portion 13 and an inner surface, the proximal portion 13 being configured to be inserted into a patient's vessel to allow a medical device 100 to be inserted through the introducer sheath 10 into the patient's vessel, and
    a dilator 20 having a body 21 with a proximal portion 23, a distal portion 22 and an outer surface, the dilator 20 being insertable into the introducer sheath 10 such that its proximal portion 23 extends proximally of the introducer sheath 10 when the dilator 20 is inserted in the introducer sheath 10, wherein the tubular body 11 of the introducer sheath has a wall thickness d of 0.3 mm or less, and wherein at least one of the dilator 20 and the introducer sheath 10 comprises a stiffening structure 25 imparting stiffness to the tubular body 11 of the introducer sheath 10, wherein said stiffening structure 25 can be released, removed or otherwise deactivated.

2. The introducer set according to para. 1, wherein the tubular body 11 of the introducer sheath 10 has a wall thickness of less than 0.2 mm, preferably less than 0.15 mm, more preferably less than 0.1 mm.

3. The introducer set according to para. 1 or 2, wherein the stiffening structure 25, when activated, causes surface friction between at least a portion of the outer surface of the dilator 20 and at least a portion of the inner surface of the tubular body 11 of the introducer sheath 10 and, when deactivated, causes less or no friction.

4. The introducer set according to para. 3, wherein, when the stiffening structure 25 is deactivated, the body 21 of the dilator 20 has a first outer diameter which is smaller than an inner diameter of the tubular body 11 of the introducer sheath 10, and wherein, when the stiffening structure 25 is activated, at least a portion, preferably at least a proximal portion 23, of the dilator 20 has a second outer diameter larger than the first outer diameter such that the outer surface of the dilator 20 contacts the inner surface of the tubular body 11 of the introducer sheath 10.

5. The introducer set according to any one of paras. 1 to 4, wherein the stiffening structure comprises a deflatable balloon 25.

6. The introducer set according to para. 5, wherein the balloon 25 is arranged at least in the proximal portion 23 of the dilator body 21, preferably along substantially an entire length of the dilator body 21.

7. The introducer set according to para. 5 or 6, wherein the dilator 20 comprises an inflation port 26 at the distal portion 22 of the dilator body 21 that is in fluid communication with the balloon 25.

8. The introducer set according to para. 7, wherein the inflation port 26 is connected to a reservoir 31 fillable with a fluid and comprising a pressure device 30, preferably a syringe-type pressure device, such that a fluid received in the reservoir 30 can be pressurized to inflate the balloon 25.

9. The introducer set according to para. 8, wherein the pressure device 30 comprises a plunger 33 which is sealed against an inner wall of the reservoir 31 and has a first thread 39, the pressure device 30 further comprising an actuating screw 32 having a second thread 38 mating with the first thread 39 such that the plunger 33 can be moved within the reservoir 31 to pressurize fluid received in the reservoir 31 by rotation of the actuating screw 32.

10. The introducer set according to any one of paras. 5 to 9, wherein the balloon 25 comprises a non-compliant material, preferably a polyamide, preferably Nylon.

11. The introducer set according to any one of paras. 1 to 4, wherein the stiffening structure comprises first and second elements 121, 122; 221, 222; 321, 322 that are translatable with respect to each other, and an actuating mechanism 123; 223; 323 for translating at least one of the first and second elements with respect to the other in a longitudinal direction of the dilator 120; 22; 320, wherein rotation of the actuating mechanism 123; 223; 323 preferably causes such longitudinal translation.

12. The introducer set according to para. 11, wherein the second element 122; 222; 322 has a tubular body and the first element 121; 221; 321 extends through the tubular body of the second element 122; 222; 322 beyond a proximal end of the first element 121; 221; 321.

13. The introducer set according to para. 11 or 12, wherein the stiffening structure comprises at least one deformable member 125; 225 engaging the first and second elements 121, 122; 221, 222 such that said longitudinal translation causes a decompression of the deformable member 125; 225; 325 in the longitudinal direction of the dilator 120; 220 and thereby a radial reduction of the deformable member 125; 225, wherein the deformable member preferably forms part of the dilator and, in an uncompressed state, has substantially the same diameter as the body of the dilator.

14. The introducer set according to para. 13, wherein the deformable member 125 is ring-shaped or tubular-shaped.

15. The introducer set according to para. 13 or 14, wherein the deformable member 125 comprises a soft polymer, preferably a silicone.

16. The introducer set according to para. 13, wherein the deformable member comprises a plurality of slits 226 extending in the longitudinal direction of the dilator 220 to allow the deformable member to radially collapse upon said longitudinal decompression.

17. The introducer set according to para. 11 or 12, wherein the stiffening structure comprises at least one deformable member 325 attached to the first element 321 and engaging the second element 322, wherein the deformable member 325 comprises a plurality of tabs 325 slidable on a ramped end portion 326 of the second element 322 to radially deform when the second element 322 is longitudinally translated.

18. The introducer set according to any one of paras. 13 to 17, wherein the deformable member 125; 225; 325 is formed separately from or integrally with at least one of the first and second elements 121, 122; 221, 222; 321, 322.

19. The introducer set according to para. 1 or 2, wherein the introducer sheath comprises a hydraulic port 426 that is in fluid communication with a space 424 defined by the inner surface of the introducer sheath and the outer surface of the dilator 420.

20. The introducer set according to any one of paras. 1 to 19, wherein the tubular body of the introducer sheath comprises at least one cavity extending in the longitudinal direction of the tubular body and accommodating a removable supporting strut.

21. The introducer set according to para. 20, wherein the supporting strut has a cross-section that is different in shape from a cross-section of the cavity to provide low friction between the cavity and the supporting strut, preferably a polygonal or star-like cross-sectional shape.

22. The introducer set according to any one of paras. 1 to 21, wherein the flexible material of the introducer sheath 10 comprises PTFE.

23. The introducer set according to any one of paras. 1 to 22, wherein the introducer sheath 10 comprises a hemostatic valve 14 at its distal portion 12.

24. The introducer set according to any one of paras. 1 to 23, wherein the introducer sheath 10 is separable along its length.

25. The introducer set according to any one of paras. 1 to 24, wherein the medical device comprises a catheter 100.

26. The introducer set according para. 25, comprising an axial blood pump 101 arranged at the tip of the catheter 100.

27. A dilator 20; 120; 220; 320 configured for use in an introducer sheath, comprising a body with an outer surface, wherein the dilator is collapsible so as to allow for decreasing a cross-section of the body in order to decrease surface friction between the outer surface and an inner surface of the introducer sheath.

28. The dilator according to para. 27, comprising a deflatable balloon 25.

29. The dilator according to para. 28, wherein the balloon 25 is arranged at least in a proximal portion 23 of the body 21, preferably along substantially an entire length of the body 21.

30. The dilator according to para. 28 or 29, comprising an inflation port 26 at a distal portion 22 of the dilator body 21 that is in fluid communication with the balloon 25.

31. The dilator according to para. 30, wherein the inflation port 26 is connected to a reservoir 31 fillable with a fluid and comprising a pressure device 30, preferably a syringe-type pressure device, such that a fluid received in the reservoir 31 can be pressurized to inflate the balloon 25.

32. The dilator according to para. 31, wherein the pressure device 30 comprises a plunger 33 which is sealed against an inner wall of the reservoir 31 and has a first thread 39, the pressure device 30 further comprising an actuating screw 32 having a second thread 38 mating with the first thread 39 such that the plunger 33 can be moved within the reservoir 31 to pressurize fluid received in the reservoir 31 by rotation of the actuating screw 32.

33. The dilator according to any one of paras. 28 to 32, wherein the balloon 25 comprises a non-compliant material, preferably a polyamide, preferably Nylon.

34. The dilator according to para. 27, comprising first and second elements 121, 122; 221, 222; 321, 322 that are translatable with respect to each other, and an actuating mechanism 123; 223; 323 for translating at least one of the first and second elements with respect to the other in a longitudinal direction of the dilator 120; 22; 320, wherein rotation of the actuating mechanism 123; 223; 323 preferably causes such longitudinal translation.

35. The dilator according to para. 34, wherein the second element 122; 222; 322 has a tubular body and the first element 121; 221; 321 extends through the tubular body of the second element 122; 222; 322 beyond a proximal end of the first element 121; 221; 321.

36. The dilator according to para. 34 or 35, comprising at least one deformable member 125; 225 engaging the first and second elements 121, 122; 221, 222 such that said longitudinal translation causes a decompression of the deformable member 125; 225; 325 in the longitudinal direction of the dilator 120; 220 and thereby a radial reduction of the deformable member 125; 225, wherein the deformable member preferably forms part of the dilator and, in an uncompressed state, has substantially the same diameter as the body of the dilator.

37. The dilator according to para. 36, wherein the deformable member 125 is ring-shaped or tubular-shaped.

38. The dilator according to para. 36 or 37, wherein the deformable member comprises a soft polymer, preferably a silicone.

39. The dilator according to para. 36, wherein the deformable member comprises a plurality of slits 226 extending in the longitudinal direction of the dilator 220 to allow the deformable member to radially collapse upon said longitudinal decompression.

40. The dilator according to para. 34 or 35, comprising at least one deformable member 325 attached to the first element 321 and engaging the second element 322, wherein the deformable member 325 comprises a plurality of tabs 325 slidable on a ramped end portion 326 of the second element 322 to radially deform when the second element 322 is longitudinally translated.

41. The dilator according to any one of paras. 36 to 40, wherein the deformable member 125; 225; 325 is formed separately from or integrally with at least one of the first and second elements 121, 122; 221, 222; 321, 322.

42. An introducer sheath comprising a tubular body made of a flexible material with a distal portion and a proximal portion, the proximal portion being configured to be inserted into a patient's vessel to allow a medical device to be inserted through the introducer sheath into the patient's vessel, wherein the tubular body has a wall thickness of 0.3 mm or less, preferably less than 0.2 mm, more preferably less than 0.15 mm, even more preferably less than 0.1 mm.

43. The introducer sheath according to para. 42, comprising a hydraulic port 426 that is in fluid communication with a space 424 defined by the inner surface of the introducer sheath and the outer surface of the dilator 420.

44. The introducer sheath according to para. 42 or 43, wherein the tubular body comprises at least one cavity extending in the longitudinal direction of the tubular body accommodating a removable supporting strut.

45. The introducer sheath according to para. 44, wherein the supporting strut has a cross-section that is different in shape from a cross-section of the cavity to provide low friction between the cavity and the supporting strut, preferably a star-like cross-sectional shape.

46. The introducer sheath according to any one of paras. 42 to 45, wherein the flexible material comprises PTFE.

47. The introducer sheath according to any one of paras. 42 to 46, comprising a hemostatic valve 14 at the distal portion 12.

48. The introducer sheath according to any one of paras. 42 to 47, wherein the introducer sheath 10 is separable along its length.

49. A method for providing vascular access in a patient's body, comprising the steps of:
providing an introducer set 1 comprising an introducer sheath 10 and a dilator 20, the introducer sheath 10 comprising a tubular body 11 with a distal portion 12, a proximal portion 13 and an inner surface, the proximal portion 13 being configured to be inserted into a patient's vessel to allow a medical device 100 to be inserted through the introducer sheath 10 into the patient's vessel, wherein the tubular body 11 of the introducer sheath 10 has a wall thickness of 0.3 mm or less, and the dilator 20 comprising a body 21 with a proximal portion 23, a distal portion 22 and an outer surface, the dilator 20 being inserted in the introducer sheath 10 such that the proximal portion 23 extends proximally out of the introducer sheath 10, wherein the dilator 20 comprises a deflatable balloon 25 for decreasing surface friction between at least a portion of the outer surface of the dilator 20 and at least a portion of the inner surface of the tubular body 11 of the introducer sheath 10,
inserting the introducer sheath 10 and the dilator 20 into a vessel of a patient,
deflating the balloon 25, and
retracting the dilator 20 from the introducer sheath 10 such that the introducer sheath 10 is left behind in the patient's vessel.

50. A method for providing vascular access in a patient's body, comprising the steps of:
providing an introducer set 1 comprising an introducer sheath 10 and a dilator 20, the introducer sheath 10 comprising a tubular body 11 with a distal portion 12, a proximal portion 13 and an inner surface, the proximal portion 13 being configured to be inserted into a patient's vessel to allow a medical device 100 to be inserted through the introducer sheath 10 into the patient's vessel, wherein the tubular body 11 of the introducer sheath 10 has a wall thickness of 0.3 mm or less, and the dilator 20 comprising a body 21 with a proximal portion 23, a distal portion 22 and an outer surface, the dilator 20 being insertable into the introducer sheath 10 such that the proximal portion 23 extends proximally out of the introducer sheath 10 when the dilator 20 is inserted in the introducer sheath 10, wherein the dilator 20 comprises a deflatable balloon 25 for decreasing surface friction between at least a portion of the outer surface of the dilator 20 and at least a portion of the inner surface of the tubular body 11 of the introducer sheath 10, inserting the dilator 20 into the introducer sheath 10, inflating the balloon 25 of the dilator 20, inserting the introducer sheath 10 and the dilator 20 into a vessel of a patient, deflating the balloon 25, and retracting the dilator 20 from the introducer sheath 10 such that the introducer sheath 10 is left behind in the patient's vessel.

The invention claimed is:

1. An introducer set for providing vascular access in a patient's body, comprising:

an introducer sheath having a tubular body with a wall thickness of 0.3 mm or less, the tubular body having a distal end, a proximal end, and an inner surface, and the proximal end being configured to be inserted into a patient's vessel; and a dilator having a dilator body with a tapered proximal end, a distal end, an outer surface, and a stiffening structure, the dilator body being insertable into the introducer sheath, wherein the stiffening structure is configured to be activated when the dilator body is inserted within the introducer sheath and at least a portion of the tapered proximal end of the dilator body extends proximally of the proximal end of the introducer sheath, causing at least a portion of the stiffening structure to expand radially and contact at least a portion of the inner surface of the introducer sheath, and wherein the stiffening structure is configured to be deactivated when the dilator body is inserted within the introducer sheath and at least a portion of the tapered proximal end of the dilator body extends proximally of the proximal end of the introducer sheath, causing the at least a portion of the stiffening structure to contract radially and reduce or eliminate contact with the at least a portion of the inner surface of the introducer sheath.

2. The introducer set of claim 1, wherein the tubular body of the introducer sheath has a wall thickness of less than 0.2 mm.

3. The introducer set of claim 2, wherein the tubular body of the introducer sheath has a wall thickness of less than 0.1 mm or less.

4. The introducer set of claim 1, wherein an inner diameter of the tubular body of the introducer sheath is at least 14 French.

5. The introducer set of claim 2, wherein an inner diameter of the tubular body of the introducer sheath is at least 14 French.

6. The introducer set of claim 3, wherein an inner diameter of the tubular body of the introducer sheath is at least 14 French.

7. The introducer set of claim 1, wherein the stiffening structure comprises a deflatable balloon.

8. The introducer set of claim 7, wherein, when the stiffening structure is activated while the dilator body is inserted within the introducer sheath and at least a portion of the tapered proximal end of the dilator body extends proximally of the proximal end of the introducer sheath, a transitional portion of the balloon extends proximally of the proximal end of the introducer sheath.

9. The introducer set of claim 8, wherein the transitional portion of the balloon is configured to create a continuous transition between the tapered proximal end of the dilator body and the proximal end of the introducer sheath.

10. The introducer set of claim 8, wherein the balloon extends from the distal end of the dilator body to a distal end of the tapered proximal end.

11. The introducer set of claim 8, wherein the dilator comprises an inflation port that is in fluid communication with the balloon.

12. The introducer set of claim 11, further comprising a pressurizing device in fluid communication with the inflation port configured to pressurize a working fluid to inflate the balloon.

13. The introducer set of claim 1, further comprising a hub coupled to the distal end of the introducer sheath, the hub comprising a hemostasis valve.

14. The introducer set of claim 13, wherein the hub is configured with one or more notches configured to allow the hub to be broken.

* * * * *